(12) United States Patent
Freidel et al.

(10) Patent No.: US 11,497,494 B2
(45) Date of Patent: Nov. 15, 2022

(54) SURGICAL STAPLER CARTRIDGE RETAINER WITH EJECTOR FEATURE

(71) Applicant: Ethicon LLC, Guaynabo, PR (US)

(72) Inventors: Scott T. Freidel, Cincinnati, OH (US); Michael E. Setser, Burlington, KY (US); Lauren M. Valente, Macomb, MI (US)

(73) Assignee: Cilag GmbH International, Zug (CH)

( * ) Notice: Subject to any disclaimer, the term of this patent is extended or adjusted under 35 U.S.C. 154(b) by 134 days.

(21) Appl. No.: 16/916,295

(22) Filed: Jun. 30, 2020

(65) Prior Publication Data
US 2021/0401433 A1   Dec. 30, 2021

(51) Int. Cl.
*A61B 17/072* (2006.01)
*A61B 17/00* (2006.01)

(52) U.S. Cl.
CPC .. *A61B 17/072* (2013.01); *A61B 2017/00477* (2013.01); *A61B 2017/0725* (2013.01); *A61B 2017/07228* (2013.01); *A61B 2017/07257* (2013.01); *A61B 2017/07278* (2013.01); *A61B 2017/07285* (2013.01)

(58) Field of Classification Search
CPC ........... A61B 2017/07271; A61B 2017/07278; A61B 2017/07214
See application file for complete search history.

(56) References Cited

U.S. PATENT DOCUMENTS

| 5,366,133 | A  | * | 11/1994 | Geiste | A61B 17/07207 227/175.1 |
|---|---|---|---|---|---|
| 6,585,144 | B2 | * | 7/2003 | Adams | A61B 17/072 227/156 |
| 7,044,352 | B2 | * | 5/2006 | Shelton, IV | A61B 17/07207 227/175.1 |
| 7,147,140 | B2 | * | 12/2006 | Wukusick | A61B 17/072 227/182.1 |
| 7,207,472 | B2 | * | 4/2007 | Wukusick | A61B 17/072 227/176.1 |

(Continued)

FOREIGN PATENT DOCUMENTS

| EP | 2932918 A1 | 10/2015 |
|---|---|---|
| EP | 3072457 A2 | 9/2016 |
| WO | WO 2018/176414 A1 | 10/2018 |

OTHER PUBLICATIONS

International Search Report and Written Opinion dated Oct. 1, 2021, for International Application No. PCT/IB2021/055793, 17 pages.

*Primary Examiner* — Gloria R Weeks
(74) *Attorney, Agent, or Firm* — Frost Brown Todd LLC

(57) ABSTRACT

An apparatus includes an elongate body, at least one latch member, and a cartridge removal feature. The elongate body is sized and shaped to correspond with a deck of a surgical staple cartridge such that the elongate body is configured to cover a plurality of staple apertures of the surgical staple cartridge. The at least one latch member is configured to removably secure the elongate body to the surgical staple cartridge. The cartridge removal feature is integral with the elongate body. The cartridge removal feature defines a gap that is configured to receive a portion of the surgical staple cartridge. The cartridge removal feature is further operable to remove the surgical staple cartridge from a surgical stapler.

20 Claims, 17 Drawing Sheets

(56) References Cited

U.S. PATENT DOCUMENTS

| | | | | |
|---|---|---|---|---|
| 7,334,717 | B2 * | 2/2008 | Rethy | A61B 17/105 227/175.1 |
| 7,404,508 | B2 | 7/2008 | Smith et al. | |
| 7,434,715 | B2 | 10/2008 | Shelton, IV et al. | |
| 7,568,604 | B2 * | 8/2009 | Ehrenfels | A61B 17/07207 227/176.1 |
| 7,721,930 | B2 | 5/2010 | McKenna et al. | |
| 8,015,976 | B2 * | 9/2011 | Shah | A61B 17/07207 128/898 |
| 8,210,411 | B2 | 7/2012 | Yates et al. | |
| 8,371,491 | B2 * | 2/2013 | Huitema | A61B 50/30 227/176.1 |
| 8,397,972 | B2 * | 3/2013 | Kostrzewski | A61B 17/068 227/175.2 |
| 8,408,439 | B2 | 4/2013 | Huang et al. | |
| 8,453,914 | B2 | 6/2013 | Laurent et al. | |
| 8,714,352 | B2 * | 5/2014 | Farascioni | A61B 50/30 206/340 |
| 9,113,881 | B2 * | 8/2015 | Scirica | A61B 90/92 |
| 9,186,142 | B2 | 11/2015 | Fanelli et al. | |
| 9,326,770 | B2 * | 5/2016 | Shelton, IV | A61B 17/07207 |
| 9,386,984 | B2 * | 7/2016 | Aronhalt | A61B 17/068 |
| 9,517,065 | B2 | 12/2016 | Simms et al. | |
| 9,622,746 | B2 * | 4/2017 | Simms | A61B 17/07207 |
| 9,706,993 | B2 * | 7/2017 | Hessler | A61B 17/072 |
| 9,717,497 | B2 | 8/2017 | Zerkle et al. | |
| 9,795,379 | B2 | 10/2017 | Leimbach et al. | |
| 9,808,248 | B2 | 11/2017 | Hoffman | |
| 10,039,546 | B2 * | 8/2018 | Williams | A61B 17/1155 |
| 10,092,292 | B2 | 10/2018 | Boudreaux et al. | |
| 10,420,551 | B2 * | 9/2019 | Calderoni | H01R 12/57 |
| 10,646,221 | B2 * | 5/2020 | Shelton, IV | A61B 17/07207 |
| 10,709,445 | B2 * | 7/2020 | Scirica | A61B 17/068 |
| 10,849,620 | B2 * | 12/2020 | Cappola | A61B 17/072 |
| 2013/0146643 | A1 * | 6/2013 | Schmid | A61B 17/0644 227/180.1 |
| 2015/0134076 | A1 * | 5/2015 | Shelton, IV | A61F 2/0077 623/23.72 |
| 2015/0190133 | A1 * | 7/2015 | Penna | A61B 50/30 227/175.2 |
| 2016/0128694 | A1 * | 5/2016 | Baxter, III | A61B 17/0686 227/178.1 |
| 2016/0249929 | A1 * | 9/2016 | Cappola | A61B 90/98 227/176.1 |
| 2018/0168643 | A1 * | 6/2018 | Shelton, IV | A61B 17/07207 |
| 2020/0261085 | A1 | 8/2020 | Boudreaux et al. | |

* cited by examiner

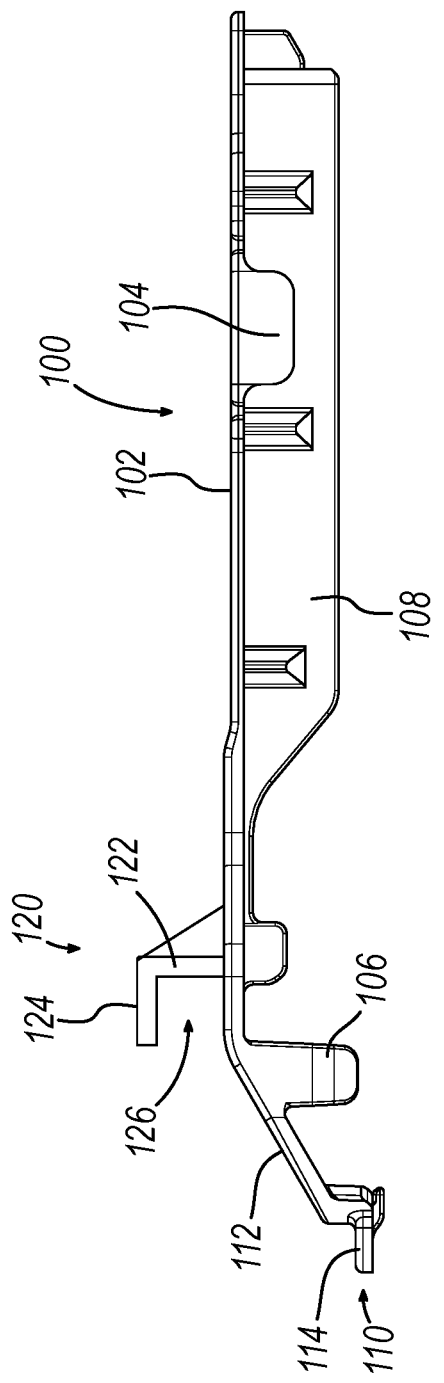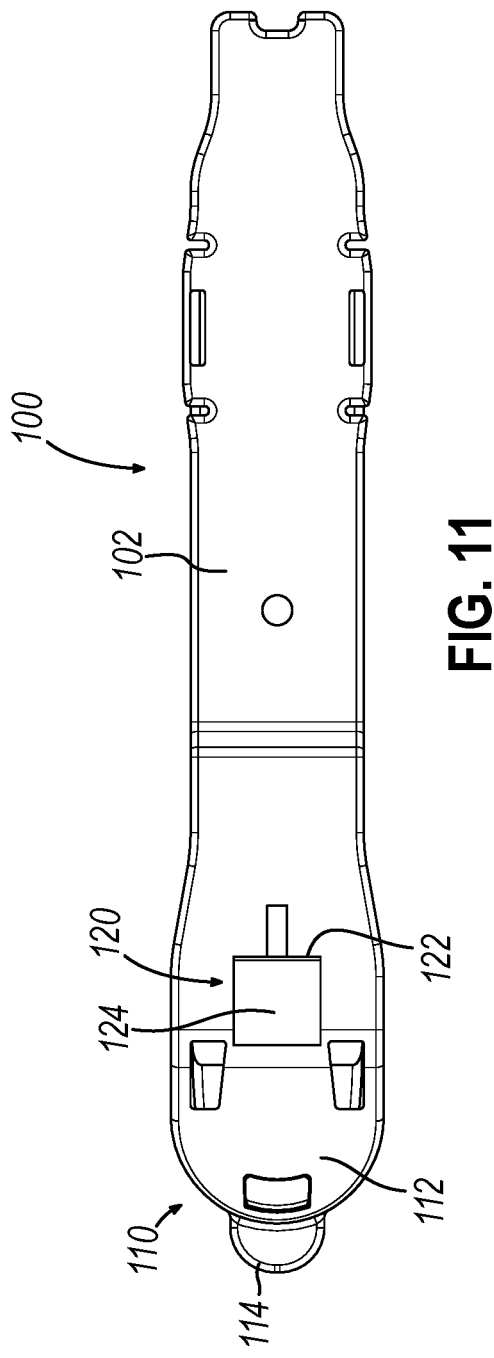

SURGICAL STAPLER CARTRIDGE RETAINER WITH EJECTOR FEATURE

BACKGROUND

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10 depicts a side elevation view of the retainer of FIG. 8;

FIG. 11 depicts a top plan view of the retainer of FIG. 8;

Figure 1:
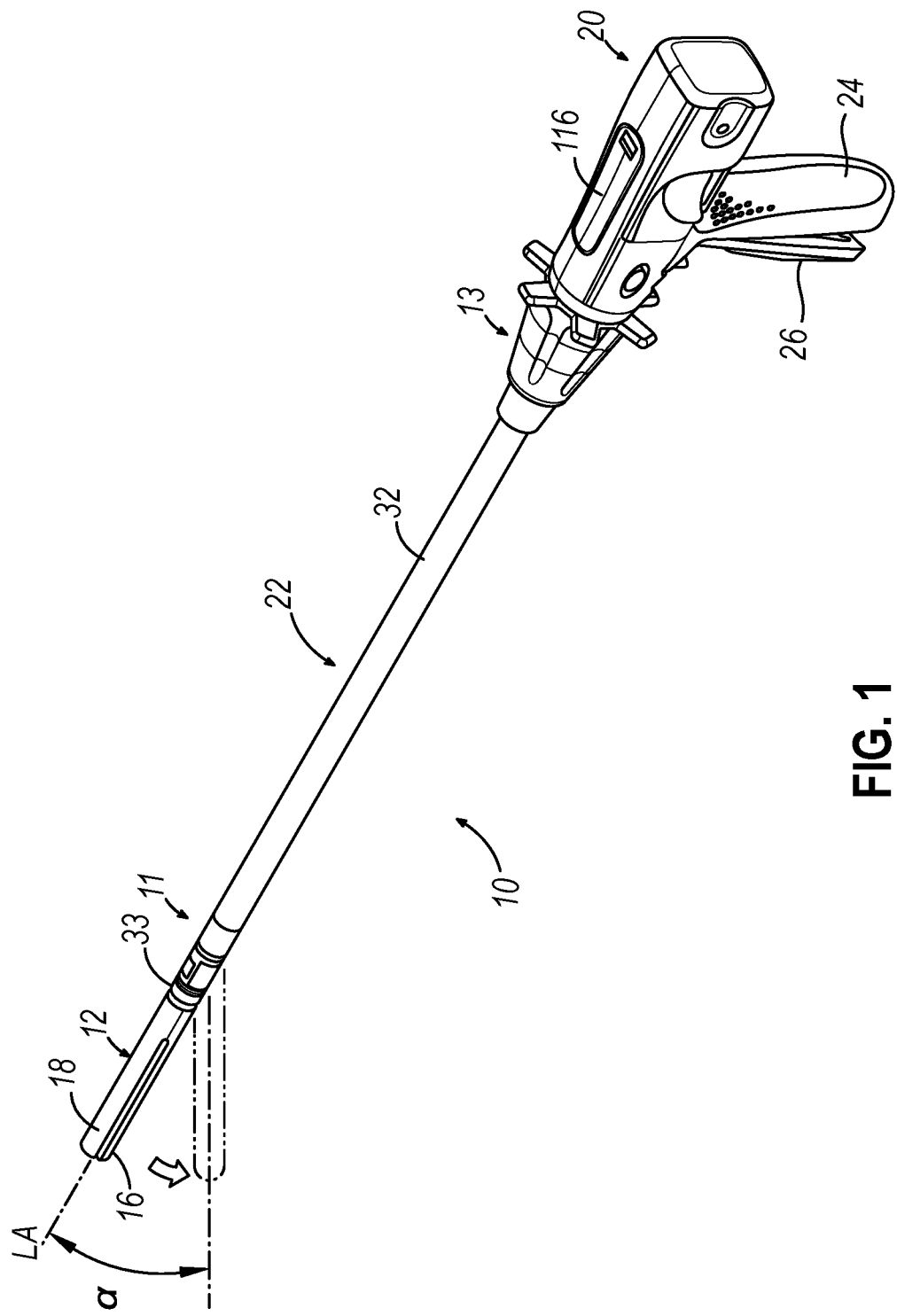
FIG. 1 depicts a perspective view of an example of an articulating surgical stapling instrument.
Figure 2:
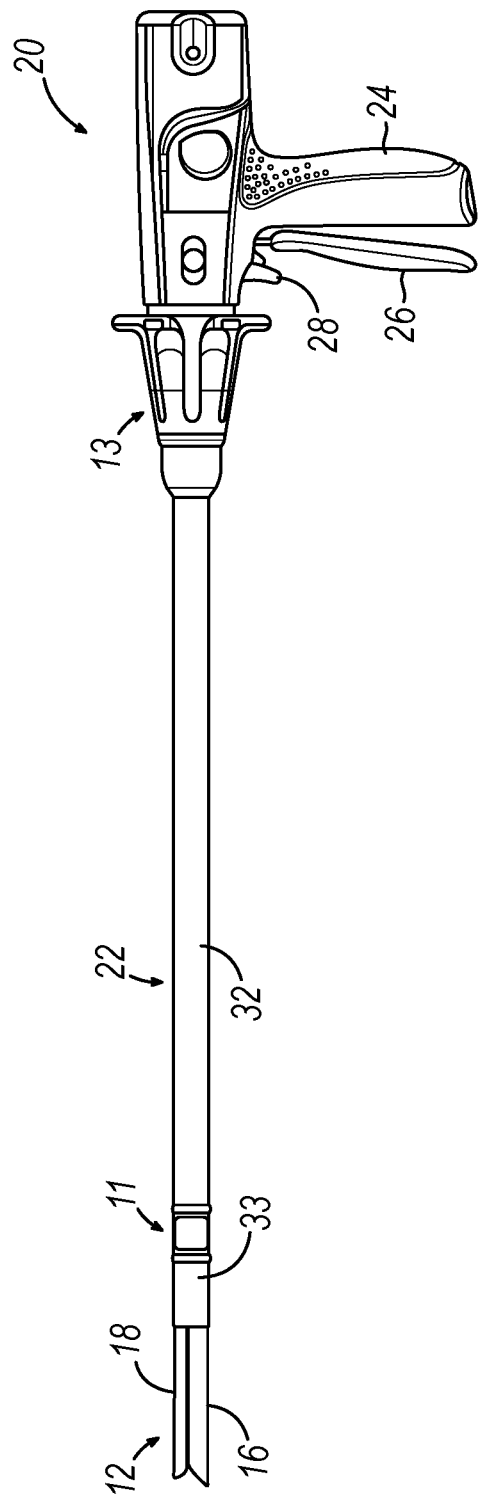
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Example of Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (a). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
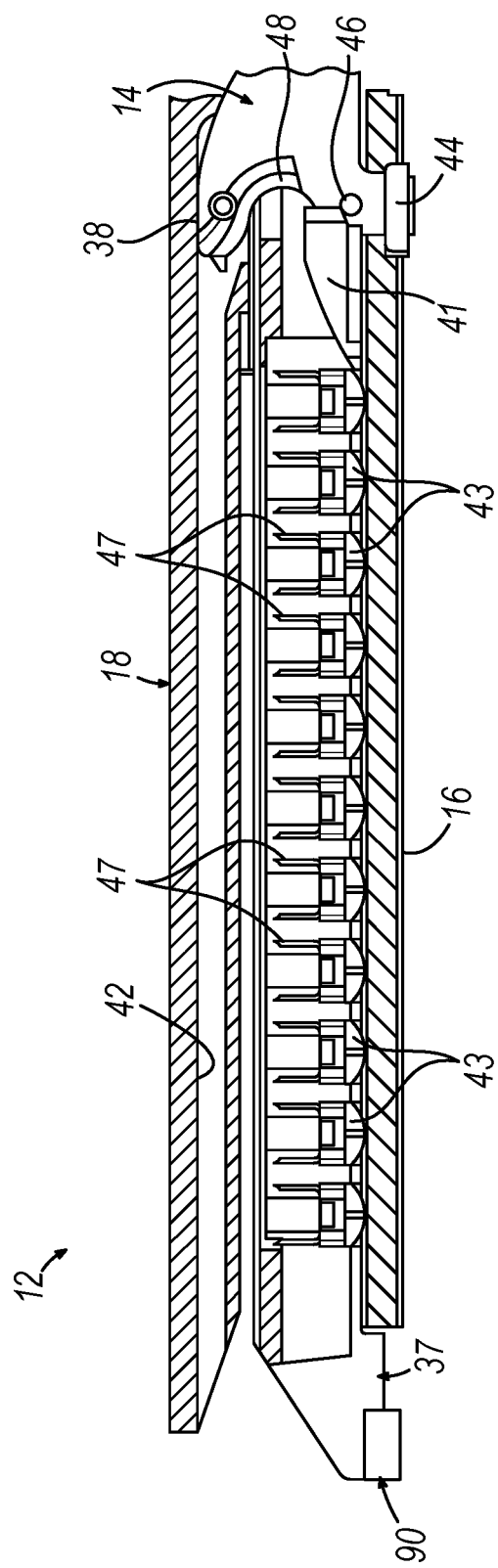
FIG. 4A depicts a side cross-sectional view of the end effector of FIG. 3, taken along line 4-4 of FIG. 3, with the firing beam in a proximal position.
Figure 4B:
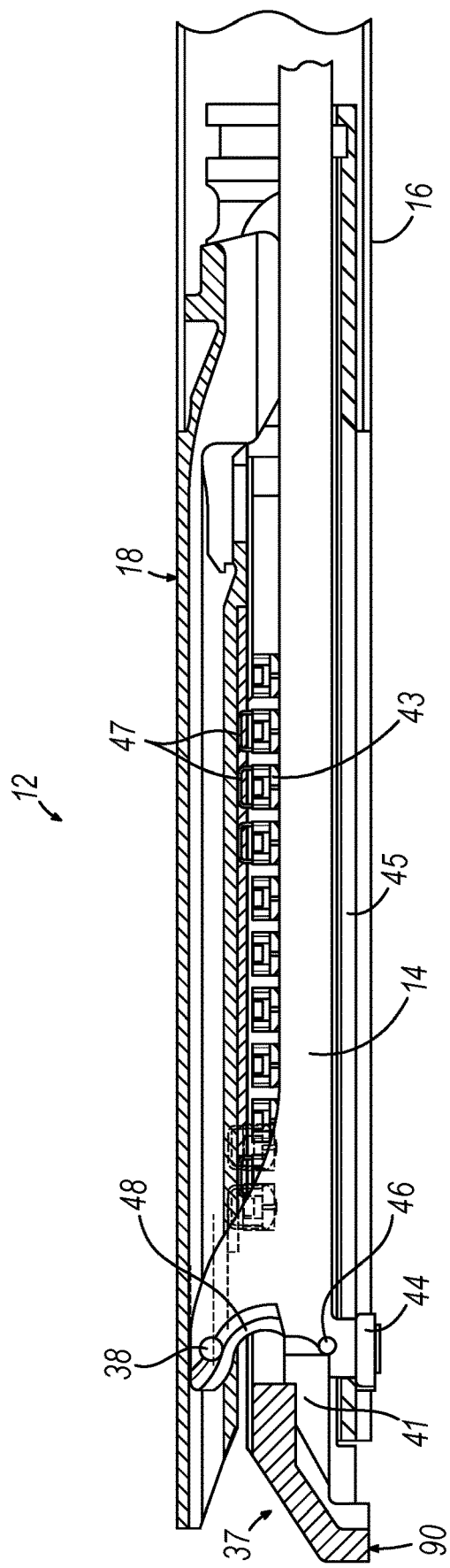
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
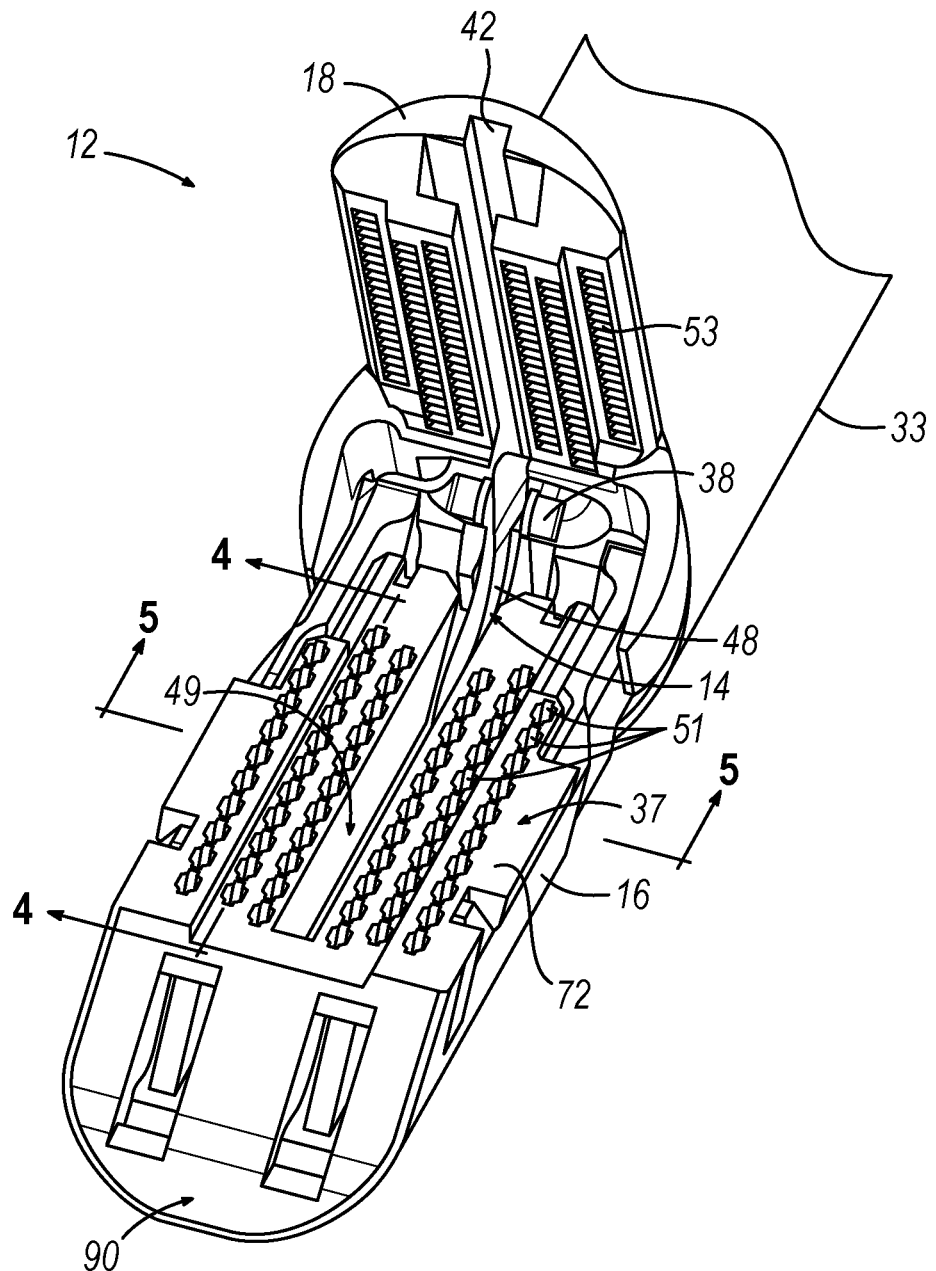
FIG. 3 depicts a perspective view of an opened end effector of the instrument of FIG. 1.
Figure 5:
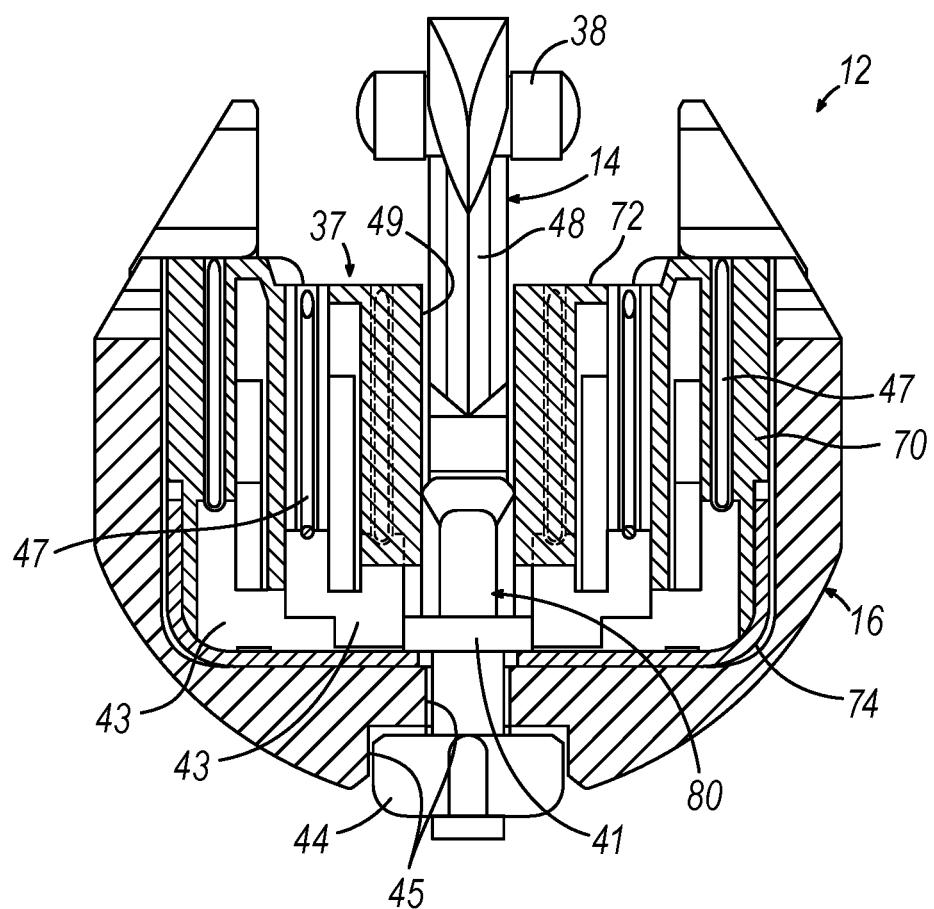
FIG. 5 depicts an end cross-sectional view of the end effector of FIG. 3, taken along line 5-5 of FIG. 3.
Figure 6:
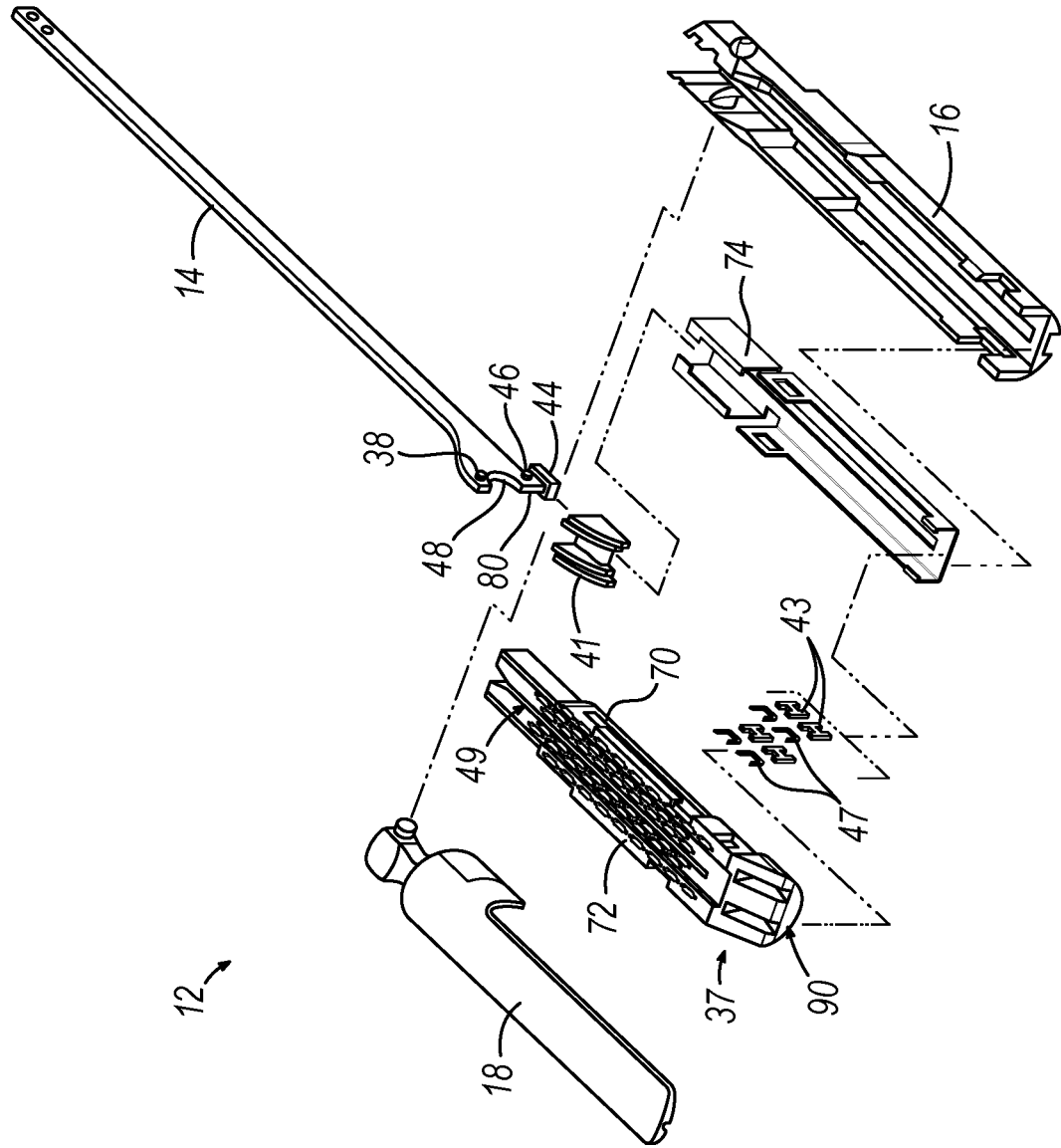
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at the distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
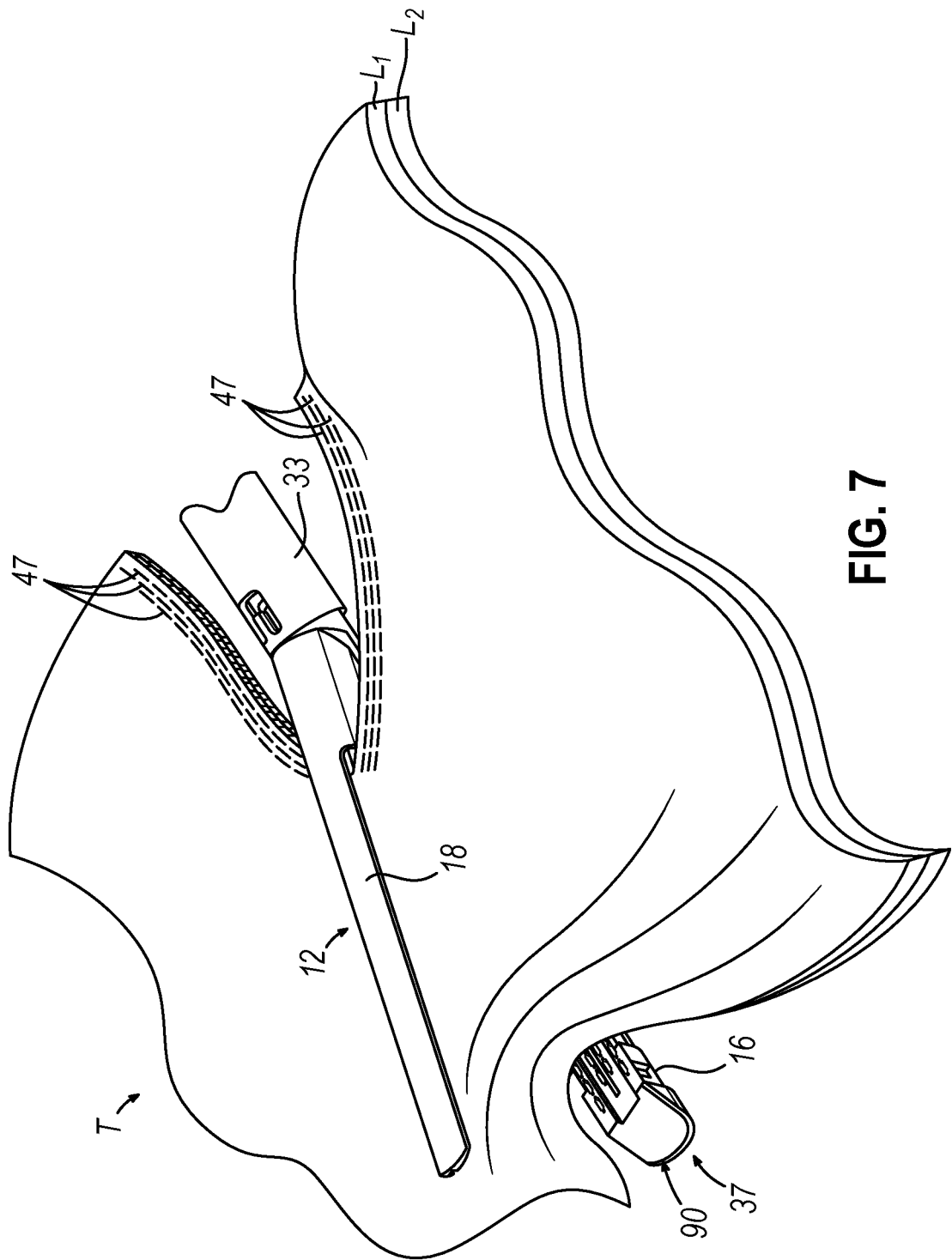
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through the tissue (T) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

II. Staple Cartridge Retainer

As noted above, staple cartridge (37) includes a plurality of staples (47) positioned in corresponding staple apertures (51). While staples (47) may be configured to provide a slight interference fit within staple apertures (51) to prevent staples (47) from inadvertently falling out of staple cartridge (37) before end effector (12) is fired to drive staples (47) into tissue, it may be desirable to provide an additional feature that helps retain staples (47) in staple apertures (51) until staple cartridge (37) is loaded into lower jaw (16) of end effector (12). To that end, FIGS. 8-11 show an example of a retainer (100) that may be temporarily secured to staple cartridge (37).

Figure 8:
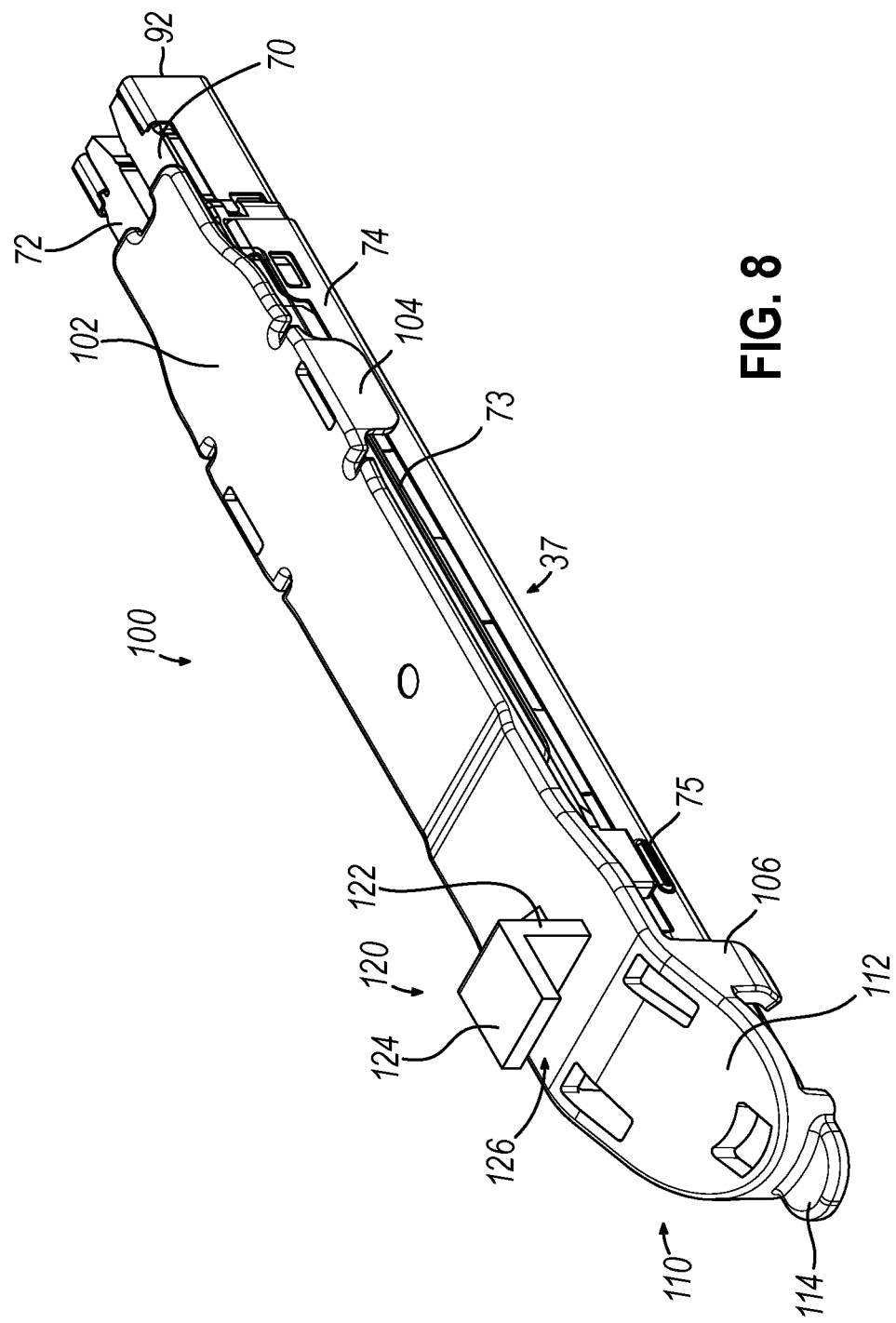
FIG. 8 depicts a perspective view of a staple cartridge of the instrument of FIG. 1, with an example of a retainer secured to the staple cartridge.

Retainer (100) of the present example includes an elongate body (102) whose width and length substantially corresponds with the width and length of staple cartridge (37). A pair of proximal latch arms (104) and a pair of distal latch arms (106) extend downwardly from body (102). Proximal latch arms (104) are configured to latch onto a longitudinally extending lateral flange (73) of cartridge body (70), as best seen in FIG. 8. Distal latch arms (106) are configured to latch onto the underside of distal end (90) of staple cartridge (37). Latch arms (104, 106) thus releasably secure retainer (100) to staple cartridge (37) through a snap fit in the present example. Alternatively, retainer (100) may be releasably secured to staple cartridge (37) in any other suitable fashion as will be apparent to those skilled in the art in view of the teachings herein.

Figure 9:
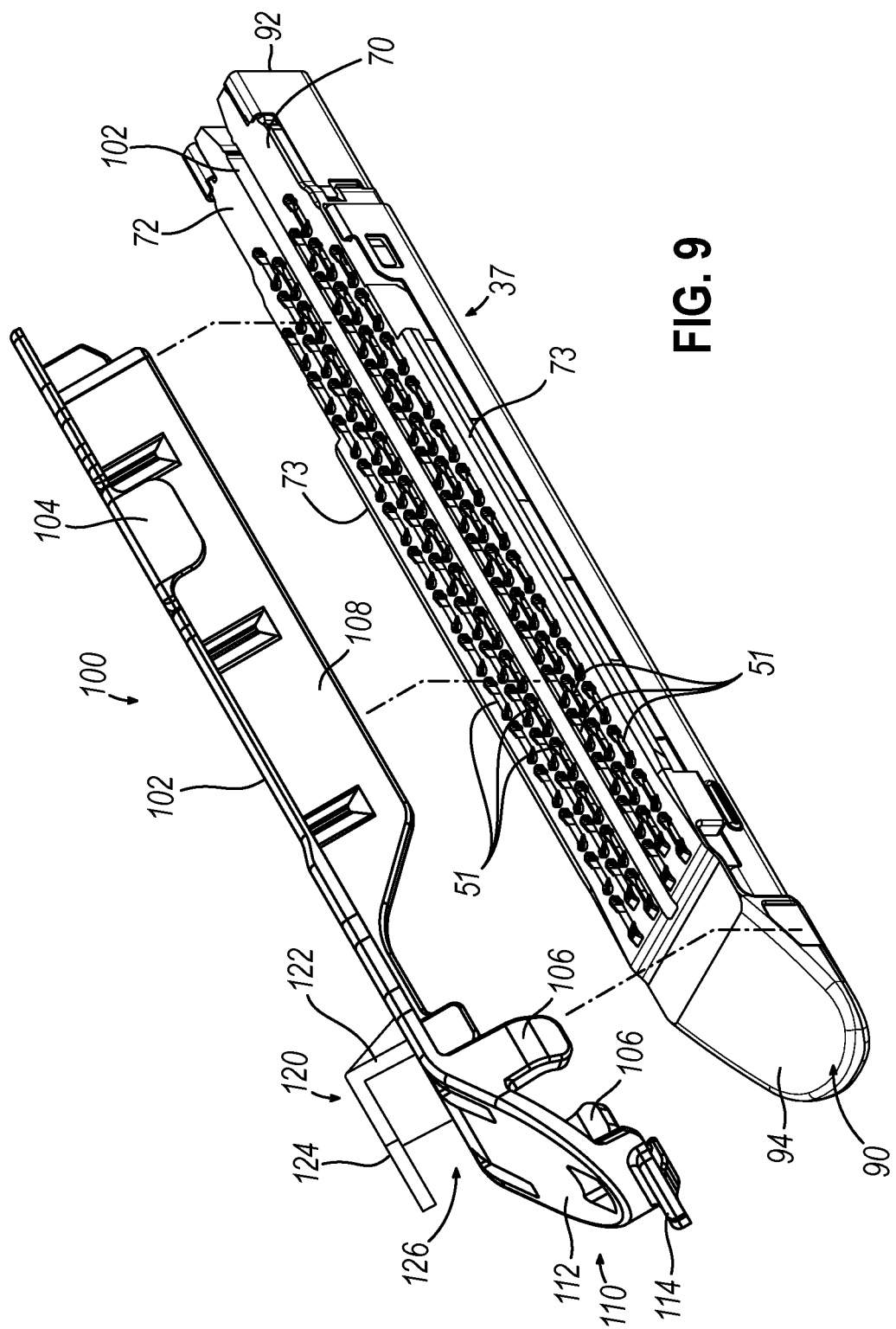
FIG. 9 depicts a perspective view of the staple cartridge and retainer of FIG. 8, with the retainer removed from the staple cartridge.

As shown in FIGS. 9-10, a fin (108) also extends downwardly from body (102). Fin (10) is configured to fit within vertical slot (49) of staple cartridge (37). By way of example only, fin (10) may promote proper alignment between retainer (100) and staple cartridge (37) while retainer (100) is being secured to staple cartridge (37). By way of further example only, fin (10) may also prevent inadvertent distal movement of wedge sled (41) through staple cartridge (37) while retainer (100) is secured to staple cartridge (37).

A distal portion (110) of retainer (100) includes an angled body (112) that is obliquely oriented relative to elongate body (102). In the present example, bodies (102, 112) are unitarily formed as a homogenous continuum of material. Angled body (112) is angled to correspond with an angle defined between a distal surface (94) of distal end (90) of staple cartridge (37) and deck (72) of staple cartridge (37). In other words, elongate body (102) is configured to correspond with and complement deck (72); while angled body (112) is configured to correspond with and complement distal end (90). A tongue (114) projects distally from angled body (112) and is configured to facilitate removal of retainer (100) from staple cartridge (37) as described in greater detail below.

In some scenarios, retainer (100) may be secured to staple cartridge (37) at a manufacturing facility and may remain secured to staple cartridge (37) as staple cartridge (37) is placed in packaging, during transit and storage of staple cartridge (37) and during removal of staple cartridge (37) from the packaging at the point of ultimate use (e.g., within an operating room). During the time that retainer (100) is secured to staple cartridge (37), elongate body (102) may prevent staples (47) from inadvertently falling out of staple cartridge (37) since elongate body (102) covers staple apertures (51).

Figure 12A:
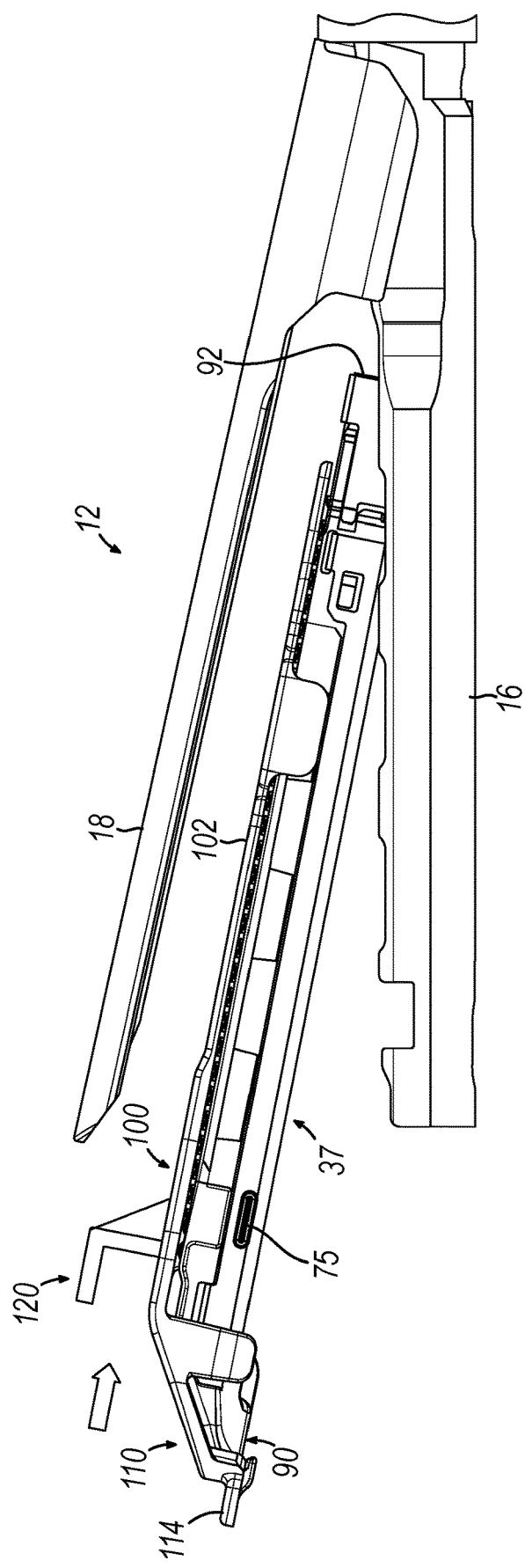
FIG. 12A depicts a side elevation view of the end effector of FIG. 3, with the staple cartridge and retainer of FIG. 8 being positioned for loading in a lower jaw of the end effector.
Figure 12B:
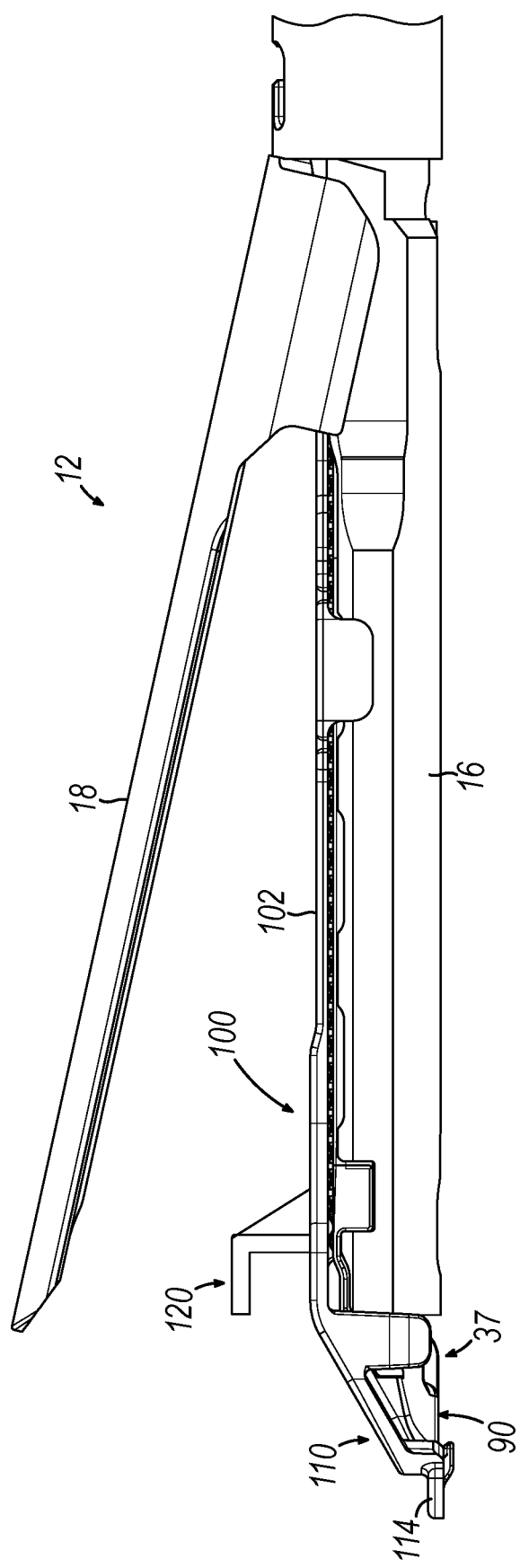
FIG. 12B depicts a side elevation view of the end effector of FIG. 3, with the staple cartridge of FIG. 8 loaded in the lower jaw of the end effector, and with the retainer of FIG. 8 still secured to the staple cartridge.
Figure 12C:
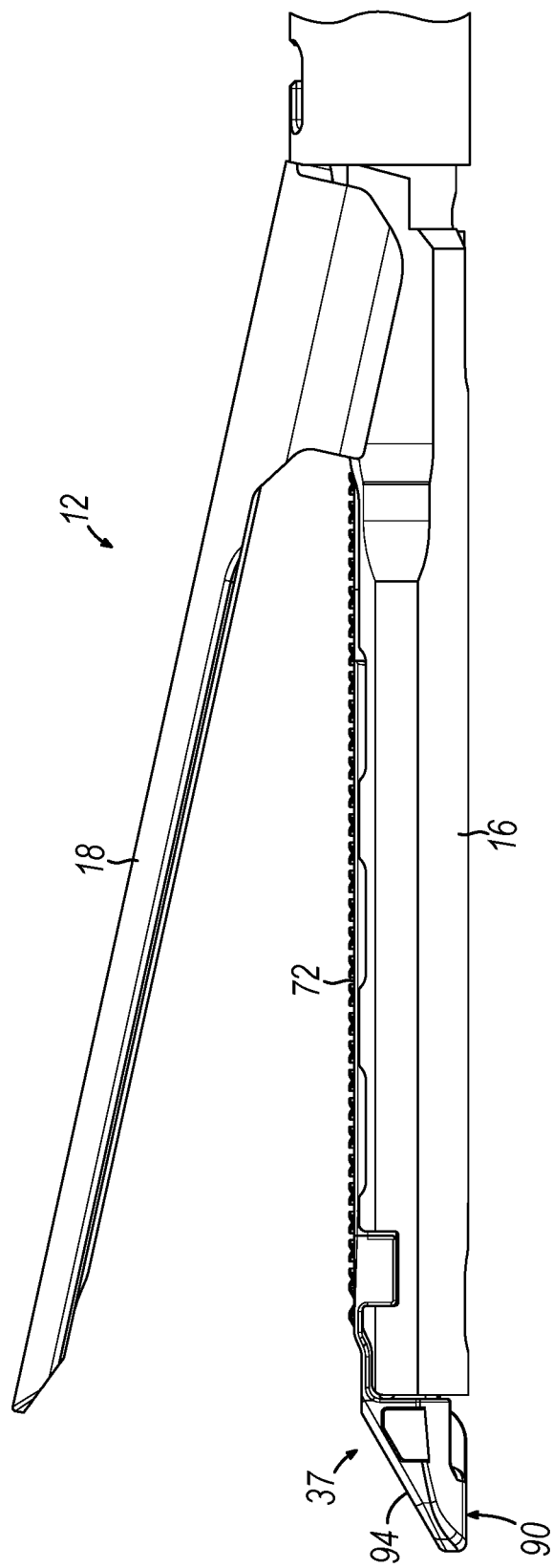
FIG. 12C depicts a side elevation view of the end effector of FIG. 3, with the staple cartridge of FIG. 8 loaded in the lower jaw of the end effector, and with the retainer of FIG. 8 removed from the staple cartridge such that the retainer is omitted from the view.

Retainer (100) may remain secured to staple cartridge (37) as staple cartridge (37) is being loaded into lower jaw (16) of end effector (12), as shown in FIGS. 12A-12C. During this process, the operator may grasp the combination of retainer (100) and staple cartridge (37) and urge proximal end (92) of staple cartridge (37) into the space between lower jaw (16) and anvil (18) as shown in FIG. 12A. When proximal end (92) of staple cartridge (37) is fully seated in end effector (12), the operator may pivot distal end (90) of staple cartridge (37) toward lower jaw (16) until staple cartridge (37) is fully seated in lower jaw (16) as shown in FIG. 12B. With staple cartridge (37) fully seated in lower jaw (16), outwardly extending detent features (75) on lateral sides of staple cartridge (37) may provide a snap fit between staple cartridge (37) and lower jaw (16), thereby removably securing staple cartridge (37) in lower jaw (16). With staple cartridge (37) thus secured in lower jaw (16), the operator may grasp tongue (114) of retainer (100) and remove retainer (100) from staple cartridge (37), leaving staple cartridge (37) secured in place in lower jaw (16) as shown in FIG. 12C. The operator may then set retainer (100) aside for later use as described below, then operate end effector (12) within the patient as described above.

As also noted above, once end effector (12) has been fired to sever tissue (T) and drive staples (47) of staple cartridge (37) into the tissue (T), it may be necessary to remove the spent staple cartridge (37) from lower jaw (16) to dispose of the spent staple cartridge (37) and perhaps replace the spent staple cartridge (37) with a new staple cartridge (37). In some instances, such as where staple cartridge (37) is secured in lower jaw (16) through a snap fit or snug fit, it may be difficult for some operators to remove the spent staple cartridge (37) from lower jaw (16). This maybe particularly so in scenarios where distal end (90) of staple cartridge (37) is the only region of staple cartridge (37) that is exposed relative to lower jaw (16) for engaging with the operator's hand. It may therefore be desirable to provide a tool that facilitates removal of a spent staple cartridge (37) from lower jaw (16). To minimize the total number of instruments in the operating room, it may be beneficial for such a cartridge (37) removal tool to be integrated into an instrument that is already in the operating room for some other purpose. To that end, retainer (100) of the present example includes an integral cartridge removal feature (120).

Cartridge removal feature (120) of this example is positioned near the distal end of elongate body (102), proximal to distal portion (110) of retainer (100). As best seen in FIGS. 8-10, cartridge removal feature (120) of this example includes a vertically extending member (122) and a distally extending member (124). Members (122, 124) cooperate to define a gap (126) between distally extending member (124) and elongate body (102). Gap (126) is sized and configured to receive distal end (90) of staple cartridge (37).

Figure 13A:
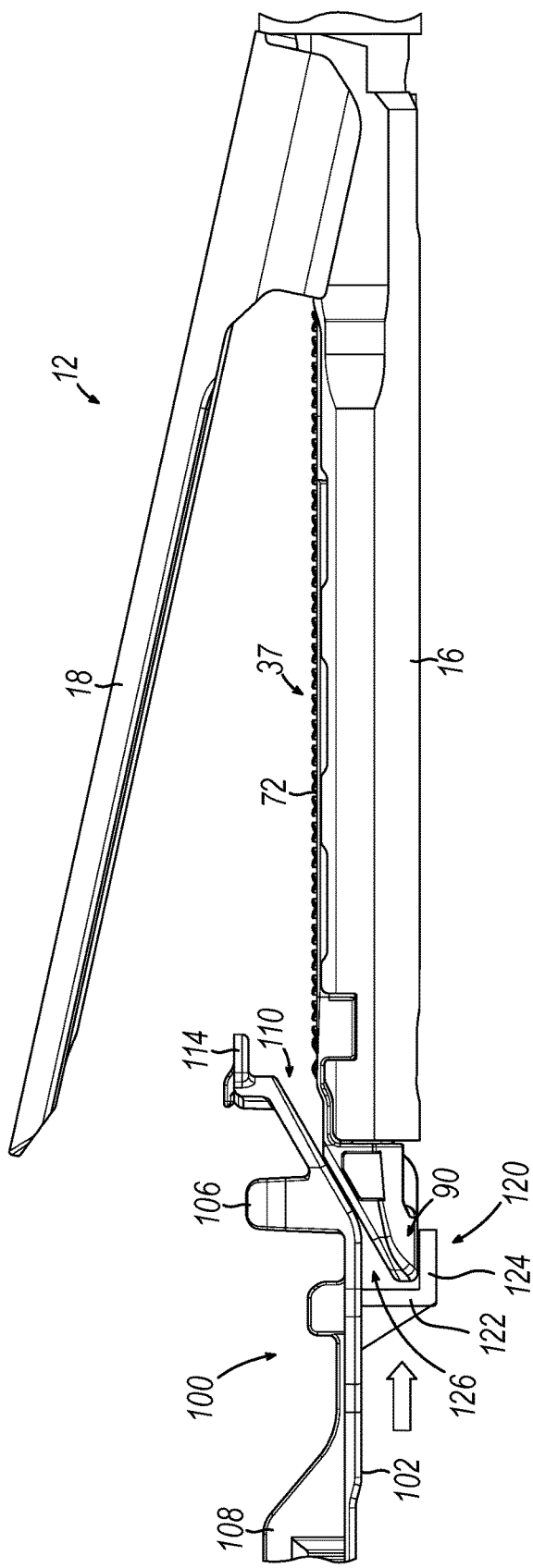
FIG. 13A depicts a side elevation view of the end effector of FIG. 3, with the retainer of FIG. 8 engaged with a distal end of the staple cartridge of FIG. 8, such that the retainer is positioned to remove the staple cartridge from the lower jaw of the end effector.
Figure 13B:
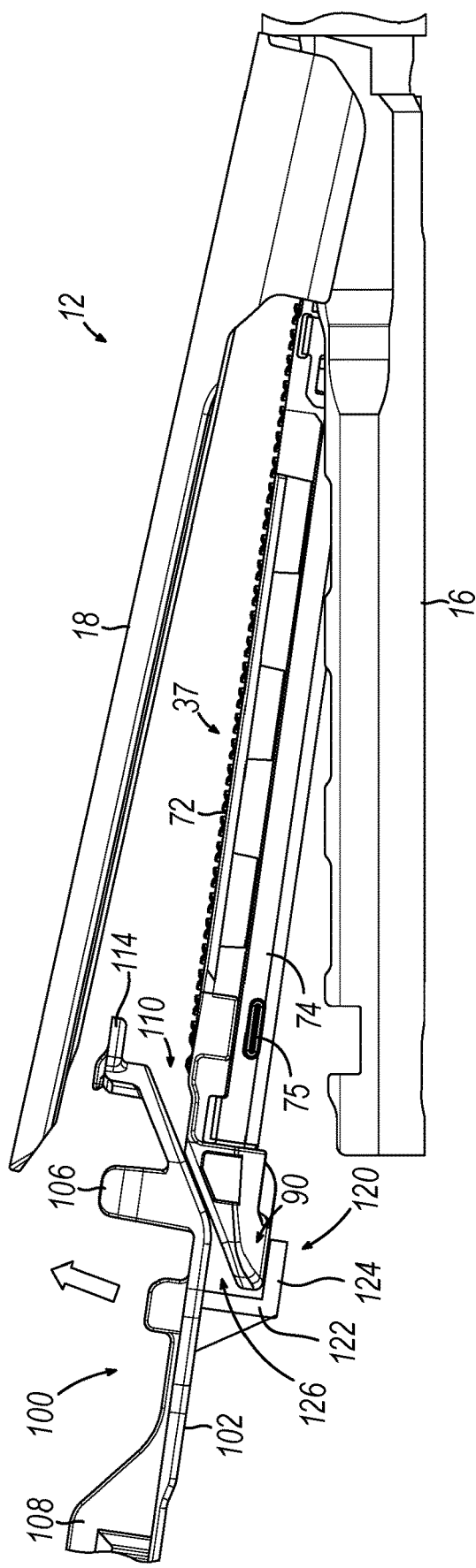
FIG. 13B depicts a side elevation view of the end effector of FIG. 3, with the retainer of FIG. 8 being used to remove the staple cartridge of FIG. 8 from the lower jaw of the end effector.
Figure 13C:
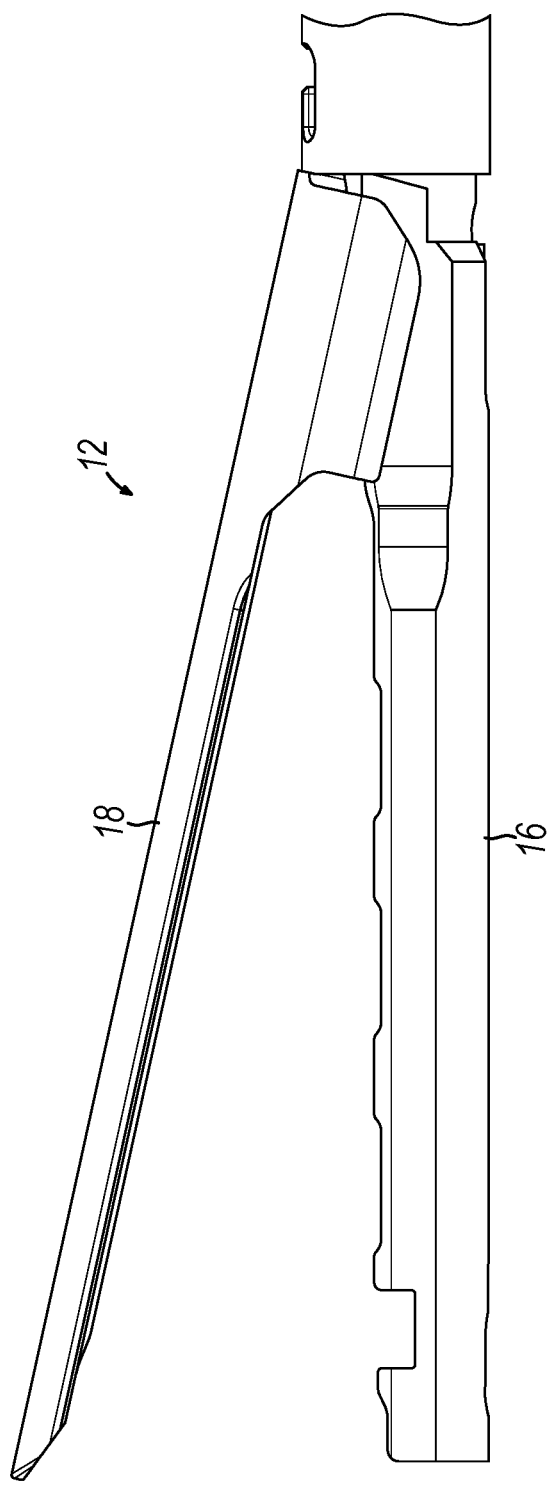
FIG. 13C depicts a side elevational view of the end effector of FIG. 3, with the staple cartridge of FIG. 8 having been removed from the lower jaw of the end effector by the retainer of FIG. 8, such that the staple cartridge and retainer are omitted from the view.

To utilize cartridge removal feature (120) of retainer (100) to remove a spent staple cartridge (37) from lower jaw (16), the operator may flip retainer upside-down and position distal end (90) of staple cartridge (37) in gap (126) as shown in FIG. 13A. The distal tip of distal end (90) may abut vertically extending member (122), the underside of distal end (90) may abut distally extending member (124), and distal surface (94) of distal end (90) may abut angled body (112). With distal end (90) appropriately seated in cartridge removal feature (120) as shown in FIG. 13A, the operator may then apply a prying motion to pivot distal end (90) away from lower jaw (16), thereby disengaging detent features (75) from lower jaw (16) as shown in FIG. 13B. The operator may then pull the combination of retainer (100) and staple cartridge (37) away from end effector (12), leaving lower jaw (16) empty as shown in FIG. 13C. The operator may then properly dispose of retainer (100) and staple cartridge (37). If desired, the operator may further load a new staple cartridge (37) with another retainer (100) into lower jaw (16) using the same process described above with reference to FIGS. 12A-12C.

In addition to facilitating removal of staple cartridge (37) from lower jaw (16), cartridge removal feature (120) may also prevent operator error where the operator might otherwise improperly attempt to secure staple cartridge (37) in lower jaw (16) by inserting cartridge (37) into end effector (12) distal end (90) first. In other words, by adding to the vertical height in the form factor at the distal region of the combination of retainer (100) and staple cartridge (37), cartridge removal feature (120) may prevent a careless or mistaken operator from getting the combination of retainer (100) and staple cartridge (37) far into end effector (12).

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an elongate body sized and shaped to correspond with a deck of a surgical staple cartridge such that the elongate body is configured to cover a plurality of staple apertures of the surgical staple cartridge; (b) at least one latch member configured to removably secure the elongate body to the surgical staple cartridge; and (c) a cartridge removal feature integral with the elongate body, the cartridge removal feature defining a gap configured to receive a portion of the surgical staple cartridge, the cartridge removal feature being further operable to remove the surgical staple cartridge from a surgical stapler.

Example 2

The apparatus of Example 1, the elongate body including an upper side and a lower side, the at least one latch member extending downwardly relative to the lower side, the cartridge removal feature extending upwardly relative to the upper side.

Example 3

The apparatus of any one or more of Examples 1 through 2, the at least one latch member including a plurality of distal latch members and a plurality of proximal latch members, the plurality of distal latch members being positioned distally in relation to the elongate body, the plurality of proximal latch members being positioned at a proximal region of the elongate body.

Example 4

The apparatus of any one or more of Examples 1 through 3, further comprising a distal portion extending distally from the elongate body, the distal portion being oriented to define an oblique angle with the elongate body.

Example 5

The apparatus of Example 4, the oblique angle being configured such that the distal portion complements and angled distal end of the surgical staple cartridge.

Example 6

The apparatus of any one or more of Examples 4 through 5, further comprising a tongue projecting distally from the distal portion, the tongue being configured to provide a grip for removal of the elongate body from the surgical staple cartridge.

Example 7

The apparatus of any one or more of Examples 4 through 6, the cartridge removal feature being positioned proximally relative to the distal portion.

Example 8

The apparatus of any one or more of Examples 1 through 7, further comprising a fin, the fin being configured to fit in a channel of the surgical staple cartridge.

Example 9

The apparatus of any one or more of Examples 1 through 8, the cartridge removal feature including a vertically extending member and a distally extending member.

Example 10

The apparatus of Example 9, the vertically extending member, the distally extending member and the elongate body cooperating to define the gap.

Example 11

The apparatus of any one or more of Examples 1 through 10, the cartridge removal feature being formed of a rigid material.

Example 12

The apparatus of any one or more of Examples 1 through 11, further comprising the surgical stapling cartridge, the surgical stapling cartridge including: (i) a deck, the staple apertures being formed through the deck, elongate body being sized and configured to fit over the deck, and (ii) a plurality of staples positioned in the staple apertures.

Example 13

The apparatus of Example 12, further comprising a surgical stapler, the surgical stapler having an end effector, the end effector including: (i) a first jaw, the first jaw being configured to removably receive the surgical stapling cartridge, and (ii) a second jaw, the second jaw including an anvil, the anvil being configured to move toward and away from the first jaw.

Example 14

The apparatus of any one or more of Examples 12 through 13, the surgical stapling cartridge further including a distal end defining an oblique angle with the deck, the gap of the cartridge removal feature being configured to receive the distal end of the surgical stapling cartridge.

Example 15

The apparatus of Example 14, further comprising an angled distal portion projecting distally and integrally from the elongate body, the angled distal portion defining an oblique angle with the elongate body, the angled distal portion being angled to complement the distal end of the surgical stapling cartridge.

Example 16

An apparatus, comprising: (a) a surgical stapling cartridge, the surgical stapling cartridge including: (i) an elongate body, the elongate body of the surgical stapling cartridge including a deck, (ii) a plurality of staple apertures formed through the deck, (iii) a plurality of staples positioned in the staple apertures, and (iv) a distal portion positioned distal to the deck; and (b) a retainer, the retainer including: (i) an elongate body, the elongate body of the retainer being sized and configured to cover the staple apertures of the deck, (ii) at least one latch member configured to removably secure the elongate body of the retainer to the elongate body of the surgical stapling cartridge, and (iii) a cartridge removal feature integral with the elongate body of the retainer, the cartridge removal feature defining a gap configured to receive the distal portion of the surgical staple cartridge, the cartridge removal feature being further operable to remove the surgical staple cartridge from a surgical stapler.

Example 17

A method comprising: (a) securing a surgical stapling cartridge in an end effector of a surgical stapler while a retainer is secured to the surgical stapling cartridge; (b) removing the retainer from the surgical stapling cartridge; (c) firing the surgical stapling cartridge; and (d) using the retainer to remove the fired surgical stapling cartridge from the end effector.

Example 18

The method of Example 17, the retainer having an upper side and a lower side, the lower side facing the surgical stapling cartridge during the act of securing the surgical stapling cartridge in the end effector, the lower side facing away from the surgical stapling cartridge during the act of using the retainer to remove the fired surgical stapling cartridge from the end effector, the method further comprising rotating the retainer to orient the lower side away from the surgical stapling cartridge.

Example 19

The method of any one or more of Examples 17 through 18, the retainer including a cartridge removal feature defining a gap, the act of using the retainer to remove the fired surgical stapling cartridge from the end effector including positioning a distal end of the fired surgical stapling cartridge in the gap.

Example 20

The method of Example 19, the act of using the retainer to remove the fired surgical stapling cartridge from the end effector further including prying the fired surgical stapling cartridge out of the end effector while the distal end of the fired surgical stapling cartridge is positioned in the gap.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an elongate body sized and shaped to cover at least a portion of an upper cartridge side of a surgical staple cartridge, wherein the upper cartridge side includes a deck having a plurality of staple apertures; and
   (b) a cartridge removal feature integral with the elongate body, the cartridge removal feature defining a gap that is partially enclosed by the elongate body and is configured to receive a distal end portion of the surgical staple cartridge while the apparatus contacts the upper cartridge side such that the apparatus is configured to pry the distal end portion from a jaw of a surgical stapler when the apparatus is moved relative to the jaw.

2. The apparatus of claim 1, further comprising at least one latch member configured to removably secure the elongate body to the surgical staple cartridge, the elongate body including an upper side and a lower side, the at least one latch member extending downwardly relative to the lower side, the cartridge removal feature extending upwardly relative to the upper side.

3. The apparatus of claim 2, the at least one latch member including a plurality of distal latch members and a plurality of proximal latch members, the plurality of distal latch members being positioned distally in relation to the elongate body, the plurality of proximal latch members being positioned at a proximal region of the elongate body.

4. The apparatus of claim 1, further comprising a distal portion extending distally from the elongate body, the distal portion being oriented to define an oblique angle with the elongate body.

5. The apparatus of claim 4, the oblique angle being configured such that the distal portion complements and angled distal end of the surgical staple cartridge.

6. The apparatus of claim 4, further comprising a tongue projecting distally from the distal portion, the tongue being configured to provide a grip for removal of the elongate body from the surgical staple cartridge.

7. The apparatus of claim 4, the cartridge removal feature being positioned proximally relative to the distal portion.

8. The apparatus of claim 1, further comprising a fin, the fin being configured to fit in a channel of the surgical staple cartridge.

9. The apparatus of claim 1, the cartridge removal feature including a vertically extending member and a distally extending member.

10. The apparatus of claim 9, the vertically extending member, the distally extending member and the elongate body cooperating to define the gap.

11. The apparatus of claim 1, further comprising the surgical stapling cartridge, the surgical stapling cartridge including:
    (i) a deck, the staple apertures being formed through the deck, the elongate body being sized and configured to fit over the deck, and
    (ii) a plurality of staples positioned in the staple apertures.

12. The apparatus of claim 11, further comprising a surgical stapler, the surgical stapler having an end effector, the end effector including:
    (i) a first jaw, the first jaw being configured to removably receive the surgical stapling cartridge, and
    (ii) a second jaw, the second jaw including an anvil, the anvil being configured to move toward and away from the first jaw.

13. The apparatus of claim 11, the surgical stapling cartridge further including a distal end defining an oblique angle with the deck, the gap of the cartridge removal feature being configured to receive the distal end of the surgical stapling cartridge.

14. The apparatus of claim 13, further comprising an angled distal portion projecting distally and integrally from the elongate body, the angled distal portion defining an oblique angle with the elongate body, the angled distal portion being angled to complement the distal end of the surgical stapling cartridge.

15. The apparatus of claim 1, wherein the cartridge removal feature is located proximal to a distal end of the elongate body.

16. An apparatus, comprising:
(a) a surgical stapling cartridge, the surgical stapling cartridge including:
  (i) an elongate body, the elongate body of the surgical stapling cartridge including a deck,
  (ii) a plurality of staple apertures formed through the deck,
  (iii) a plurality of staples positioned in the staple apertures, and
  (iv) a distal portion positioned distal to the deck; and
(b) a retainer, the retainer including:
  (i) an elongate body, the elongate body of the retainer being sized and configured to cover the staple apertures of the deck,
  (ii) at least one latch member configured to removably secure the elongate body of the retainer to the elongate body of the surgical stapling cartridge, and
  (iii) a cartridge removal feature integral with the elongate body of the retainer, the cartridge removal feature cooperating with the elongate body to define a gap configured to receive the distal portion of the surgical staple cartridge such that the retainer is operable to remove the surgical staple cartridge from a jaw of a surgical stapler without contacting the jaw with the cartridge removal feature.

17. A method comprising:
(a) securing a surgical stapling cartridge in an end effector of a surgical stapler while a retainer is secured to the surgical stapling cartridge;
(b) removing the retainer from the surgical stapling cartridge;
(c) firing the surgical stapling cartridge; and
(d) using the retainer to remove the fired surgical stapling cartridge from the end effector without contacting the end effector with the retainer.

18. The method of claim 17, the retainer having an upper side and a lower side, the lower side facing the surgical stapling cartridge during the act of securing the surgical stapling cartridge in the end effector, the lower side facing away from the surgical stapling cartridge during the act of using the retainer to remove the fired surgical stapling cartridge from the end effector, the method further comprising rotating the retainer to orient the lower side away from the surgical stapling cartridge.

19. The method of claim 18, the retainer including a cartridge removal feature extending from the upper side in a direction away from the lower side and defining a gap, the act of using the retainer to remove the fired surgical stapling cartridge from the end effector including positioning a distal end of the fired surgical stapling cartridge in the gap such that the distal end contacts the upper side of the retainer and an underside of the cartridge removal feature.

20. The method of claim 19, the act of using the retainer to remove the fired surgical stapling cartridge from the end effector further including prying the fired surgical stapling cartridge out of the end effector while the distal end of the fired surgical stapling cartridge is positioned in the gap.

* * * * *